(12) United States Patent
Petersilka et al.

(10) Patent No.: US 9,047,696 B2
(45) Date of Patent: Jun. 2, 2015

(54) METHOD FOR RECONSTRUCTING CT IMAGES WITH SCATTER CORRECTION, IN PARTICULAR FOR DUAL-SOURCE CT DEVICES

(71) Applicant: SIEMENS AKTIENGESELLSCHAFT, Munich (DE)

(72) Inventors: Martin Petersilka, Adelsdorf (DE); Karl Stierstorfer, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 84 days.

(21) Appl. No.: 13/779,925

(22) Filed: Feb. 28, 2013

(65) Prior Publication Data
US 2013/0259344 A1    Oct. 3, 2013

(30) Foreign Application Priority Data
Mar. 28, 2012   (DE) .......................... 10 2012 204 980

(51) Int. Cl.
*G06K 9/00* (2006.01)
*G06T 11/00* (2006.01)
*A61B 6/00* (2006.01)

(52) U.S. Cl.
CPC ............. *G06T 11/003* (2013.01); *G06T 11/006* (2013.01); *G06T 2211/408* (2013.01); *A61B 6/507* (2013.01); *G06T 11/005* (2013.01)
USPC .......................................... 382/131; 382/128

(58) Field of Classification Search
CPC ................ G06T 11/003; G06T 11/006; G06T 2211/408; G01N 21/474
USPC ......................................................... 382/128
See application file for complete search history.

(56) References Cited

U.S. PATENT DOCUMENTS

| 6,504,892 B1 * | 1/2003 | Ning | ................................. 378/4 |
| 7,015,477 B2 * | 3/2006 | Gunter | .......................... 250/369 |

(Continued)

FOREIGN PATENT DOCUMENTS

| CN | 1475000 A | 2/2004 |
| CN | 1596828 A | 3/2005 |

(Continued)

OTHER PUBLICATIONS

A general framework and review of scatter correction methods in x-ray cone-beam computerized tomography. Part 1: Scatter compensation approaches Ernst-Peter Rühmschopf and Klaus Klingenbeck; E.-P. Rührnschopf et al. A general framework and review of scatter correction methods in x-ray cone-beam computerized tomography. Part 1: Scatter compensation approaches Med. Phys. 38 (7), Jul. 2011, pp. 4296-4311; 2011.

(Continued)

*Primary Examiner* — Tom Y Lu
(74) *Attorney, Agent, or Firm* — Harness, Dickey & Pierce, P.L.C.

(57) ABSTRACT

A method is disclosed for reconstructing image data of an examination object from measurement data, wherein the measurement data were acquired in the course of a relative rotational movement between a radiation source of a computed tomography system and the examination object. First image data of the examination object are reconstructed from the measurement data. Scatter signals are calculated from the first image data using a scattered radiation model, wherein the scattered radiation model specifies an angle-dependent scatter distribution for a scatter point as a function of a line integral corresponding to an attenuation integral of a scattered beam from the scatter point to a specific detector element. The calculated scatter signals are used for correcting the measurement data, and second image data are reconstructed using the corrected measurement data.

21 Claims, 4 Drawing Sheets

(56) References Cited

U.S. PATENT DOCUMENTS

| | | |
|---|---|---|
| 7,372,936 B2 | 5/2008 | Nukui |
| 7,418,073 B2 * | 8/2008 | Schlomka et al. ............... 378/6 |
| 7,463,712 B2 * | 12/2008 | Zhu et al. ......................... 378/7 |
| 7,580,499 B2 * | 8/2009 | Van Stevendaal et al. ........ 378/7 |
| 7,680,241 B2 | 3/2010 | David |
| 8,107,589 B2 * | 1/2012 | Sakurai et al. ................. 378/65 |
| 8,238,649 B2 * | 8/2012 | Stanton et al. ................ 382/154 |
| 2003/0138074 A1 | 7/2003 | Bruder |
| 2005/0251418 A1 | 11/2005 | Kirsch |
| 2006/0153328 A1 | 7/2006 | Schlomka et al. |
| 2007/0140410 A1 | 6/2007 | Bontus |
| 2007/0242797 A1 | 10/2007 | Stewart et al. |
| 2008/0240340 A1 | 10/2008 | Bruder |
| 2009/0161818 A1 | 6/2009 | Sakurai et al. |
| 2011/0103543 A1 | 5/2011 | Flohr |
| 2012/0213424 A1 | 8/2012 | Flohr |

FOREIGN PATENT DOCUMENTS

| | | |
|---|---|---|
| CN | 1711561 A | 12/2005 |
| CN | 102048551 A | 5/2011 |
| DE | 102007014829 B3 | 9/2008 |
| JP | 2009148494 A | 7/2009 |

OTHER PUBLICATIONS

A general framework and review of scatter correction methods in cone beam CT. Part 2: Scatter estimation approaches; E.-P. Rührnschopf et al.: "A general framework and review of scatter correction methods in cone beam CT. Part 2: Scatter estimation approaches", Med. Phys. 38 (9), Sep. 2011, Am. Assoc. Phys. Med. p. 5186-5199; 2011; Sep. 1, 2011.

German Priority application No. 102012204980.0 filed. Mar. 28, 2012.

Chinese Office Action and English translation thereof dated Nov. 2, 2014.

* cited by examiner

METHOD FOR RECONSTRUCTING CT IMAGES WITH SCATTER CORRECTION, IN PARTICULAR FOR DUAL-SOURCE CT DEVICES

PRIORITY STATEMENT

The present application hereby claims priority under 35 U.S.C. §119 to German patent application number DE 10 2012 204 980.0 filed Mar. 28, 2012, the entire contents of which are hereby incorporated herein by reference.

FIELD

At least one embodiment of the invention generally relates to a method for reconstructing image data of an examination object from measurement data, the measurement data having been acquired in the course of a relative rotational movement between a radiation source of a computed tomography system and the examination object.

BACKGROUND

Tomographic imaging methods are characterized in that internal structures of an examination object can be investigated without the need for invasive interventions to be performed on the object. A possible type of tomographic image generation resides in the acquisition of a number of projections of the object to be examined from different angles. A two-dimensional sectional image (slice) or a three-dimensional volume image of the examination object can be computed from the projections.

Computed tomography is one example of such a tomographic imaging method. Methods for scanning an examination object by way of a CT system are generally known. For example, typical methods employed in such cases are circular scans, sequential orbital scans with patient feedthrough, or helical scans. Other types of scan that are not based on circular movements are also possible, such as e.g. scans using linear segments. Absorption data of the examination object are acquired from different recording angles with the aid of at least one x-ray source and at least one oppositely located detector, and the thus collected absorption data or projections are computed by way of appropriate reconstruction methods into sectional images or slices through the examination object.

In order to reconstruct computed tomographic images from x-ray CT datasets of a computed tomography device (CT scanner), i.e. from the acquired projections, a method referred to as filtered back-projection (FBP) is currently employed as the standard procedure. Following the data acquisition a so-called "rebinning" step is normally performed in which the data generated by way of the beam spreading out from the source in the shape of a fan are reordered in such a way that the data are present in a form as if the detector had been impinged upon by x-ray beams converging in parallel onto the detector. The data are then transformed into the frequency domain. Filtering takes place in the frequency domain and subsequently the filtered data are back-transformed. A back-projection onto the individual voxels within the volume of interest is then performed with the aid of the thus re-sorted and filtered data. On account of the approximate mode of operation of conventional FBP methods, however, there are problems with so-called low-frequency cone beam artifacts and helical artifacts. Furthermore, in conventional FBP methods the image sharpness is coupled to the image noise. The higher the sharpness attained, the higher also is the image noise, and vice versa.

The FBP method belongs to the group of approximate reconstruction methods. There also exists the group of exact reconstruction methods, though these are hardly used at the present time. The iterative methods, finally, form a third group of reconstruction methods.

A problem occurring more and more as the number of detector rows increases, i.e. with increasing detector width, is scattered radiation. It is namely possible that an x-ray quantum, instead of being absorbed by the examination object, is scattered, i.e. deflected in terms of its direction. This means that a specific detector element also measures x-ray quanta which do not originate from the beam which connects the x-ray source to the respective detector element. This effect is referred to as forward scattering. It leads to undesirable artifacts in the reconstructed CT images.

There also exist CT devices having two x-ray sources, called dual-source devices. If both x-ray tube assemblies are operated with the same x-ray spectrum, this increases the temporal resolution of the CT images considerably. This is because the data acquisition time is halved owing to the two x-ray sources. This is desirable in particular in the case of moving examination objects. On the other hand it is also possible to operate the two x-ray sources at different acceleration voltages and consequently with different x-ray spectra, such that a dual-energy scan is performed. This enables meaningful conclusions to be drawn concerning the composition of the recorded tissue.

The presence of scattered radiation is a well-known problem in the case of dual-source scans also. In addition to the above-described forward scattering, cross scattering also occurs with dual-source devices. This means that radiation of an x-ray source which is scattered at the surface or on the inside of the examination object arrives at the detector which is not assigned to the x-ray source. This is undesirable because only the evaluation of the transmitted radiation of the x-ray source assigned to the respective detector is relevant.

SUMMARY

At least one embodiment of the invention is directed to a method for reconstructing CT images wherein it is aimed to reduce the undesirable effects of scattered radiation. A corresponding computing unit, a CT system, a computer program and a computer-readable data medium are also to be disclosed.

A method, as well as a computing unit, a CT system, a computer program and a computer-readable data medium are disclosed. Advantageous embodiments and developments are the subject matter of dependent claims.

In at least one embodiment of the inventive method for reconstructing image data of an examination object from measurement data, the measurement data were acquired previously in the course of a relative rotational movement between a radiation source of a computed tomography system and the examination object. First image data of the examination object are reconstructed from the measurement data. Scatter signals are calculated from the first image data using a scattered radiation model. In this case the scattered radiation model specifies an angle-dependent scatter distribution for a scatter point as a function of a line integral corresponding to an attenuation integral of a scattered beam from the scatter point to a specific detector element. The calculated scatter signals are used for correcting the measurement data. Second image data are reconstructed using the corrected measurement data.

BRIEF DESCRIPTION OF THE DRAWINGS

The invention is explained in more detail below with reference to an exemplary embodiment taken in conjunction with the accompanying figures, in which.

Figure 1:
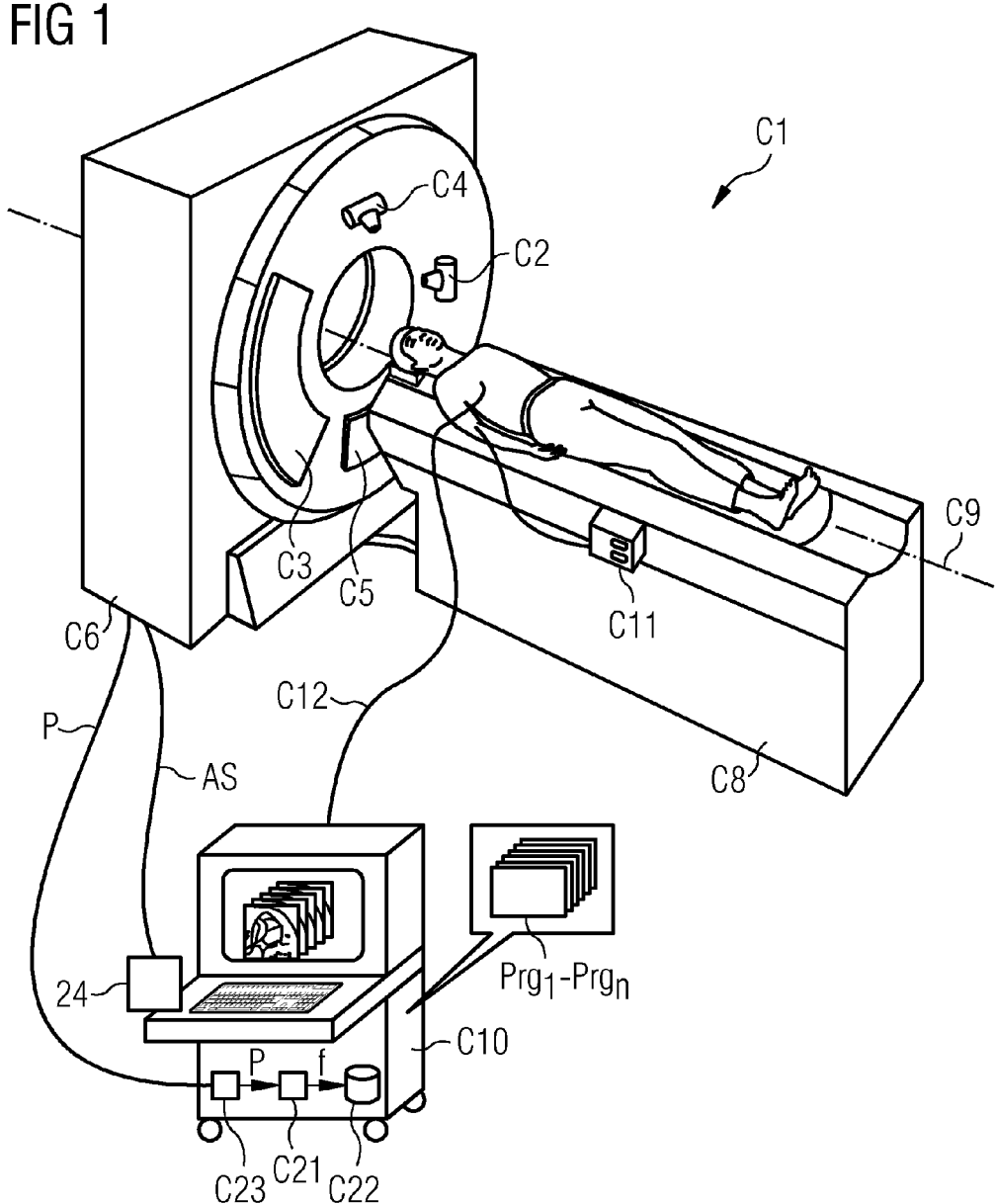
FIG. 1: shows a first schematic view of an example embodiment of a computed tomography system having an image reconstruction component.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In at least one embodiment of the inventive method for reconstructing image data of an examination object from measurement data, the measurement data were acquired previously in the course of a relative rotational movement between a radiation source of a computed tomography system and the examination object. First image data of the examination object are reconstructed from the measurement data. Scatter signals are calculated from the first image data using a scattered radiation model. In this case the scattered radiation model specifies an angle-dependent scatter distribution for a scatter point as a function of a line integral corresponding to an attenuation integral of a scattered beam from the scatter point to a specific detector element. The calculated scatter signals are used for correcting the measurement data. Second image data are reconstructed using the corrected measurement data.

Thus, a computational scattered radiation correction of the measurement data takes place. The scatter signals are calculated using a scattered radiation model which can already be determined in advance, i.e. before the measurement on the examination object is carried out. The scattered radiation model considers one scatter point and describes its scatter behavior as a function of at least two variables. The first variable is a line integral, while the second variable is the scatter angle.

The line integral indicates how strongly a beam is attenuated along the respective line; it is obtained by integration of the usually location-dependent attenuation coefficient along the line. The attenuation is due in this case to scattering and absorption. The line runs on the shortest path from the scatter point to a specific element of the detector. The detectors employed in computed tomography are typically embodied in planar form, so they include a plurality of detector elements arranged in a matrix-like array. Preferably the specific detector element is that detector element on which the scattered beam is incident at a 90° angle. This is beneficial in particular when properties of the detector are already incorporated into the scattered radiation model, e.g. the fact that beams are most likely to be detected if they strike the detector surface approximately at a 90° angle. However, it is also possible to use a different detector element, e.g. one on which the scattered beam is incident at a specific angle, instead of the detector element on which the scattered beam stands perpendicularly.

The dependence on the second variable, the angle, indicates the extent to which radiation at the scatter point is scattered in a particular direction. This angle can be an angle in the sectional plane through the examination object at a 90° angle to the z-axis, or a solid angle.

After the first image data have been computed, they can be used to correct the measurement data. With the aid of the scattered radiation model it is calculated which scatter signals will be received by the detector. For this purpose the two variables of the scattered radiation model can be assigned values in accordance with the first image data of the examination object and consequently the resulting scatter signals can be obtained. The second image data are improved in comparison with the first image data because they exhibit fewer imaging artifacts caused by the scattered radiation. Both the first and the second image data can be two-dimensional sectional images or three-dimensional volume images of the examination object.

In a development of at least one embodiment of the invention, a line integral corresponding to an attenuation integral of a beam from the respective scatter point to the respective detector element is calculated and assigned to an angle-dependent scatter distribution of the scattered radiation model in order to calculate the scatter signal for a detector element for each scatter point of the examination object using the first image data. This procedure is preferably repeated for each detector element, and per detector element for each scatter point of the examination object. A scatter point in this context is not a point having no extension, but rather a two-dimensional or three-dimensional section of the examination object, which is to say a pixel or voxel.

Furthermore, it is then possible to add together the detector-element-related contributions of the scatter distribution of a plurality of scatter points of the examination object. Preferably the contributions of all the scatter points are added. Because an angle-dependent scatter distribution has been determined per scatter point, the contribution related to a particular detector element can be found by considering the respective angle value at which the detector element is located in relation to the scatter point in the distribution curve. In the addition of the contributions a weighting can be applied as a function of the respective distance between the scatter point and the detector element. This enables greater consideration to be given e.g. to scatter points located closer to the respective detector element.

It is particularly advantageous if the scattered radiation model is determined using a model-like examination object. A suitable object in this case may be e.g. a water-filled cylinder. Alternatively hereto, other shapes and materials can also be used.

In an embodiment of the invention, the scattered radiation model is determined using a Monte Carlo simulation. Toward that end it is possible to consider a specific point of the model-like examination object and simulate how strongly the point scatters in different directions as a function of the line integral between scatter point and detector element. As an alternative to the simulation, the scattered radiation model can be determined using measurements taken on the model-like examination object.

In a development of at least one embodiment of the invention scatter signals are calculated from the second image data using the scattered radiation model, after which the calculated scatter signals are used for correcting the measurement data, and whereupon third image data are reconstructed using the corrected measurement data. This corresponds to an iterative image calculation. In this way either the third image data can be output as the result image or further image data can be calculated.

It is particularly advantageous if, according to the scattered radiation model of at least one embodiment, the angle-dependent scatter distribution additionally depends on further variables. Suitable alternative or complementary candidates for this include:

the angle between the beam incident at the scatter point and the beam scattered to the specific detector element;

the fan angle of the beam incident at the scatter point within a bundle of rays emitted by the radiation source;

the angle between the beam scattered to the specific detector element and a beam standing at a 90° angle to the center of the detector;

a line integral corresponding to an attenuation integral of the beam incident at the scatter point up to the scatter point;

a relation between the line integral corresponding to an attenuation integral of the scattered beam from the scatter point to the specific detector element and a line integral corresponding to an attenuation integral of the scattered beam from the scatter point to a different detector element;

the attenuation value of the scatter point according to the first image data;

at least one attenuation value of the material surrounding the scatter point according to the first image data.

The application of at least one embodiment of the invention to dual-source devices is particularly advantageous. This means that the measurement data were acquired in the course of a simultaneous relative rotational movement between a first radiation source and the examination object and a second radiation source and the examination object, and the scatter signals are calculated in relation to two detectors assigned to the respective radiation sources. This results in a reduction not only in the detrimental effects caused by forward scattering, but also in those due to cross scattering.

The computing unit according to at least one embodiment of the invention is used for reconstructing image data of an examination object from measurement data of a CT system. It has program segments/modules for performing the described method. In particular it can include a program memory for storing program code, there being present herein—possibly inter alia—program code that is suitable for executing a method of the above-described type, or for initiating or controlling the execution. The computing unit can also be realized by way of a plurality of interconnected devices located at different sites. This is equivalent to a distribution of the functionality of the computing unit across multiple components. It is advantageous if the computing unit is additionally capable of controlling a measurement operation performed by the CT system.

The CT system according to at least one embodiment of the invention includes such a computing unit. It may also contain other components which are required e.g. for acquiring measurement data.

The computer program according to at least one embodiment of the invention possesses program code which is suitable for performing the method of the above-described type when the computer program is executed on a computer.

The computer-readable data medium according to at least one embodiment of the invention stores program code of a computer program in order to perform the described method when the computer program is executed on a computer.

FIG. 1 firstly shows a schematic view of a first computed tomography system C1 having an image reconstruction apparatus C21. In the present example the system is a third-generation CT device, though the invention is not limited thereto. Contained within the gantry housing C6 is a closed gantry (not visible here) on which are arranged a first x-ray tube C2 and an oppositely disposed detector C3. Optionally the CT system shown here includes a second x-ray tube C4 with an oppositely disposed detector C5, such that a higher temporal resolution can be achieved by way of the additionally available emitter/detector combination; alternatively, when different x-ray energy spectra are used in the emitter/ detector systems, it also possible to perform "dual energy" examinations. In this case the CT device is a dual-source device.

The CT system C1 additionally includes a patient couch C8 on which a patient can be moved in the course of the examination along a system axis C9, also referred to as the z-axis, into the field of view. It is, however, also possible for the scanning itself to take place as a pure circular scan exclusively in the examination region of interest, without the patient being moved forward. The movement of the patient couch C8 relative to the gantry is effected by a suitable motorization device. During the movement x-ray source C2 or C4 rotates around the patient in each case. At the same time the detector C3 or C5 co-rotates in parallel opposite the x-ray source C2 or C4, respectively, in order to acquire projection measurement data which are then used for reconstructing sectional images.

Alternatively to a sequential scan, in which the patient is moved incrementally through the examination field between the individual scans, it is of course also possible to perform a helical scan, in which the patient is moved continuously along the system axis C9 through the examination field between x-ray tube C2 and C4 and detector C3 and C5 during the circumferential scan by way of the x-ray radiation. In a helical scan the movement of the patient along the axis C9 and the simultaneous revolution of the x-ray source C2 or C4 result in the x-ray source C2 or C4 traveling along a helical path relative to the patient during the measurement. The same path can also be achieved by the displacement of the gantry along the axis C9 while the patient remains stationary. It is furthermore possible to move the patient back and forth continuously and where necessary periodically between two points.

The CT system C1 is controlled by way of a control and computing unit C10 having computer program code Prg1 to Prgn resident in a memory. It is pointed out that the computer program codes Prg1 to Prgn can of course also be contained on an external storage medium and be loaded as necessary into the control and computing unit C10.

Acquisition control signals AS can be transmitted from the control and computing unit C10 via a control interface 24 in order to control the CT device in accordance with specific measurement protocols. The acquisition control signals AS relate here to e.g. the x-ray tubes C2 and C4, enabling parameters concerning the power output and the times of their activation and deactivation to be specified, as well as to the gantry, enabling parameters concerning its speed of rotation to be specified, as well as to the table feedthrough.

The control and computing unit C10 possesses an input console, enabling a user or operator of the CT device to enter measurement parameters which then, in the form of acquisition control signals AS, control the data acquisition. Information about currently used measurement parameters can be presented on the screen of the control and computing unit C10; other information relevant to the operator can be displayed in addition.

The projection measurement data P or raw data acquired by the detector C3 and/or C5 are passed to the control and computing unit C10 via a raw data interface C23. The raw data P are then processed further, possibly after suitable preprocessing, in an image reconstruction component C21. In the present exemplary embodiment the image reconstruction component C21 is realized in the control and computing unit C10 in the form of software on a processor, e.g. in the form of one or more of the computer program codes Prg1 to Prgn. In relation to the image reconstruction the same applies as explained already in relation to the control of the measurement process, i.e. that the computer program codes Prg1 to Prgn may also be contained on an external storage medium and can be loaded as necessary into the control and computing unit C10. It is furthermore possible for the control of the measurement process on the one hand and the image reconstruction on the other hand to be performed by different computing units.

The image data f reconstructed by the image reconstruction component C21 are then stored in a memory C22 of the control and computing unit C10 and/or output in the conventional manner on the screen of the control and computing unit C10. It can also be fed via an interface not shown in FIG. 1 into a network connected to the computed tomography system C1, for example a radiological information system (RIS), and stored in a mass storage facility accessible there or output as images.

In addition the control and computing unit C10 can also perform the function of an EKG, a cable C12 being used to derive the EKG potentials between patient and control and computing unit C10. In addition the CT system C1 shown in FIG. 1 also possesses a contrast agent injector C11 by way of which contrast agent can additionally be injected into the patient's bloodstream so that e.g. the vessels of the patient, in particular the ventricles of the beating heart, can be better visualized. This also affords the possibility of carrying out perfusion measurements, for which the proposed method is likewise suitable.

In contrast to its depiction in FIG. 1, the control and computing unit C10 obviously does not have to be located in proximity to the rest of the components of the CT system C1. Rather it is possible to accommodate the unit in a different room or at a more remote location. The raw data P and/or the acquisition signals AS and/or the EKG data can be transmitted over a hardwired link or alternatively wirelessly.

Figure 2:
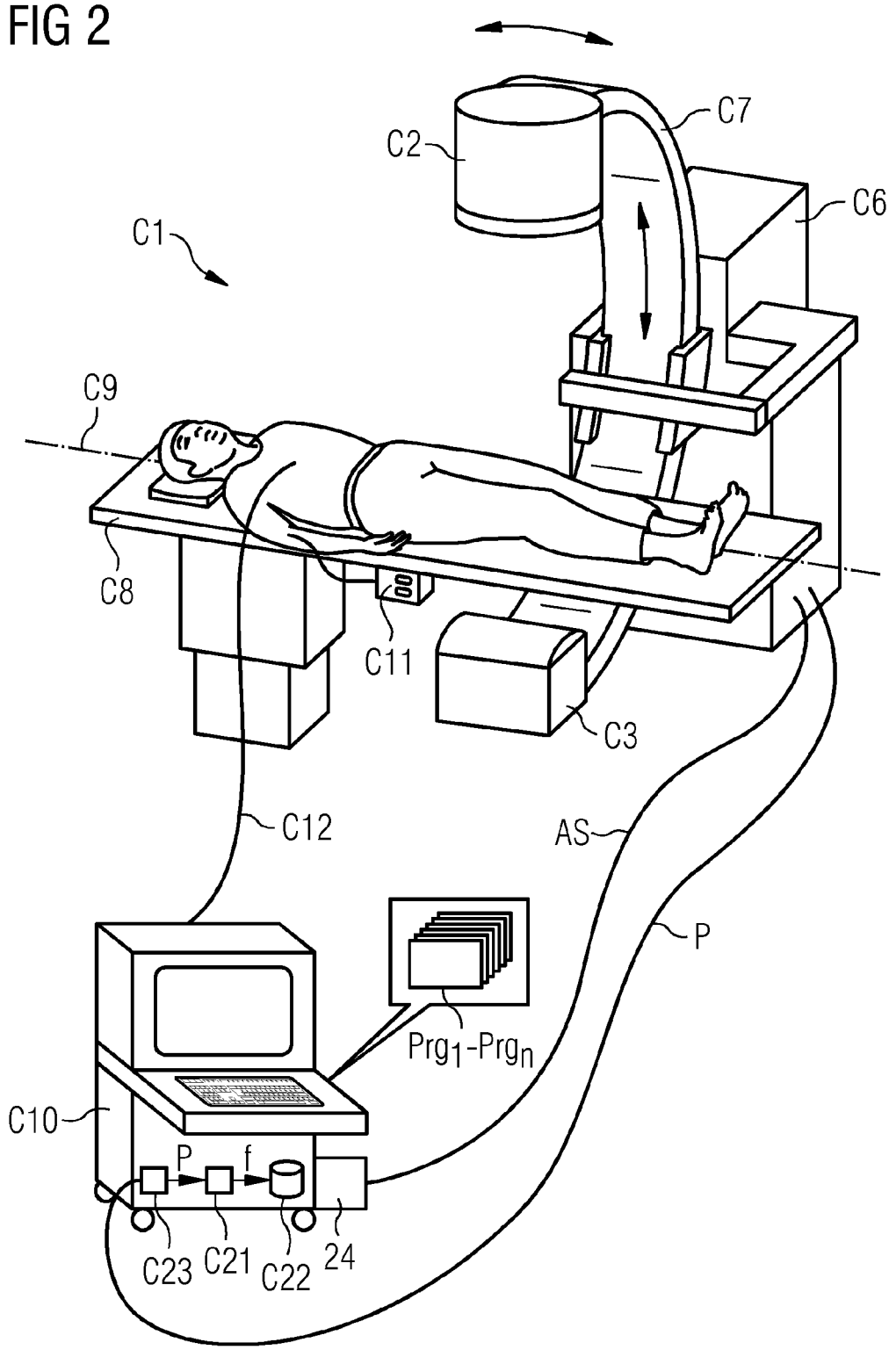
FIG. 2: shows a second schematic view of an example embodiment of a computed tomography system having an image reconstruction component.

FIG. 2 shows a C-arm system in which, in contrast to the CT system of FIG. 1, the housing C6 carries the C-arm C7, to which are secured the x-ray tube C2 on one side and the oppositely disposed detector C3 on the other side. For scanning purposes the C-arm C7 is likewise swiveled about a system axis C9, such that a scan can take place from a plurality of scanning angles and corresponding projection data P can be acquired from a plurality of projection angles. The C-arm system C1 of FIG. 2, like the CT system from FIG. 1, also comprises a control and computing unit C10 of the type described with reference to FIG. 1.

At least one embodiment of the invention can be used in both of the systems shown in FIGS. 1 and 2. Moreover, it is also suitable in principle for use in other CT systems, e.g. for CT systems having a detector forming a complete ring.

For CT devices having detectors extended in the patient's longitudinal direction, i.e. in the z-direction, one factor among others limiting the image quality is the scattered radiation due to forward scattering. Forward scattering means that an x-ray quantum is not absorbed in the examination object, but is scattered by undergoing a change in direction, and then arrives at the detector belonging to the x-ray source. This is disadvantageous because the x-ray quantum is "thrown off track" due to the scattering and consequently is measured in the wrong detector element. For purposes of image reconstruction, only those x-ray quanta are desired which arrive at the respective detector element from the x-ray source in accordance with a straight beam. Consequently, an x-ray quantum which has not moved over a straight path of the type because its direction has been changed due to scattering is incorrect information for image reconstruction purposes.

The forward scattering increases approximately linearly with the z-coverage of the detector. The reason for this is that as the width of the scanned slice increases—this corresponds to the z-coverage of the detector—the probability of an x-ray quantum being scattered in the examination object increases.

The scattered radiation causes artifacts in the images. In particular dark zones, broad, dark streaks and cupping effects, i.e. dishes or indentations, can be observed in the reconstructed images. In other words the scattered radiation does not cause a uniform deterioration over the entire image. The reason for this is that the scattering does not take place consistently, but is dependent on the attenuation of the tissue. It furthermore degrades the contrast rendering in the images.

Figure 3:
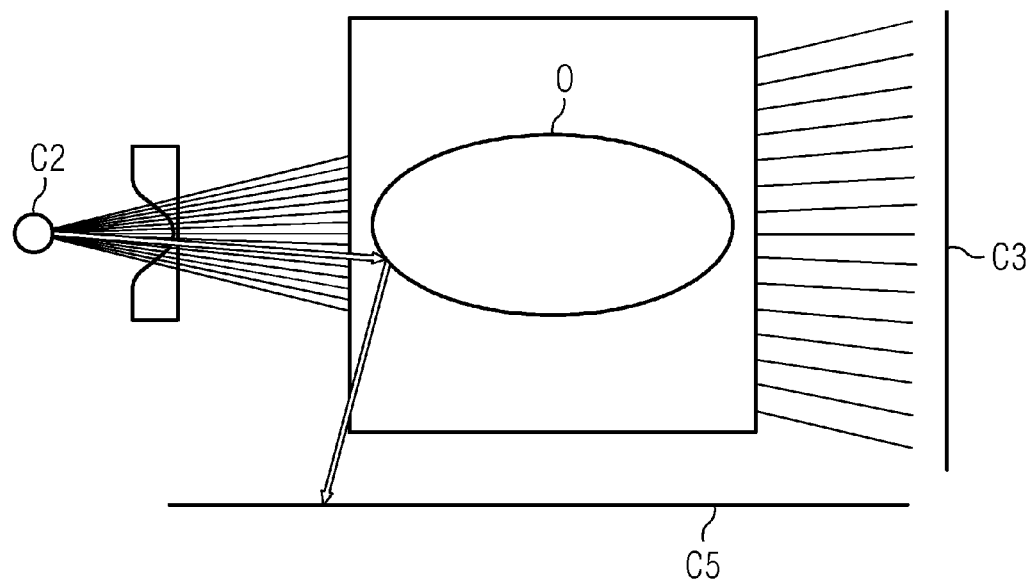
FIG. 3: shows a dual-source CT data acquisition with cross scattering.

In the case of dual-source CT devices forward scattering is accompanied by cross scattering, as illustrated with reference to FIG. 3. FIG. 3 shows a section through the acquisition geometry at a 90° angle to the z-axis. The two x-ray sources C2 and C4 can be seen, as well as the respective oppositely disposed detectors C3 and C5. For simplicity, the detectors C3 and C5 are each represented as a line. This line corresponds to a detector row having a plurality of detector elements or pixels. Further detector rows may be present adjacently in the z-direction (and consequently cannot be seen in the diagram).

The radiation of the x-ray source C2 penetrates the examination object O and reaches the detector C3, and the radiation of the x-ray source C4 penetrates the examination object O and reaches the detector C5. The cross scattering occurs in the examination object O particularly in proximity to its surface. The arrow symbolizes a beam which travels from the x-ray source C2, strikes the surface of the examination object O, and from there is scattered almost at right angles. The cross scattering is detected by the detector C5, which actually serves for measuring the radiation from the x-ray source C4.

Collimators are typically used on the detector side in order to reduce the scattered radiation. These are metal plates which are mounted in front of the detector and serve to allow through only x-ray beams from a specific direction to the respective detector element. As the z-coverage of the detector increases, and consequently the beam scatter intensity, the shaft ratio of the collimators, in other words the ratio of the height of the metal plates to the width of the detector element, must be increased in order to achieve the same effectiveness, which approach quickly reaches technological limits. Particularly problematic in this context is the mechanical stability of the collimator plates, since these must not be induced into vibration even at maximum rotation frequencies. The use of grid-like collimators, which collimate both in the image plane and in the z-direction, affords better scattered beam suppression, but is complicated and expensive. All in all, collimators are limited in terms of their effectiveness, technically complex and expensive.

Furthermore, the use of scattered beam collimators is a method in which beams are absorbed which have already penetrated the examination object and hence contribute to the dosage. Scattered beam collimators alone therefore cannot solve the scattered beam problem in the case of single-source CT devices having a detector extended in the z-direction and in particular in the case of dual-source CT devices. With dual-source CT devices there is the added problem compared with single-source CT devices that in the case of a cross-scattered x-ray quantum the direction from which the x-ray quantum strikes the wrong detector may be the right one from the collimator's perspective, so that it cannot be blocked by the collimator.

Computational scattered beam corrections are a further method for reducing the scattered radiation. With these, the scattered radiation signal is first determined for each detector element. This determination of the scattered radiation signal can be carried out e.g. by direct measurement. For the purposes of the measurement, additional detector elements can be mounted in the z-direction outside of the detector, where appropriate on both sides of the detector. This approach is also suitable for a multi-row detector because the scattered radiation in the z-direction hardly varies. If two x-ray sources are present it is alternatively possible to switch off one of the x-ray sources briefly in each case during the measurement operation in order to measure the scattered radiation directly at the respective associated detector.

Figure 4:
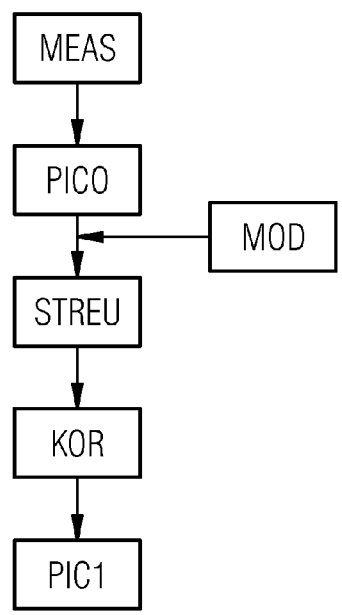
FIG. 4: is a flowchart for reconstructing image data with scatter correction.

As an alternative to measuring the scattered radiation, the latter can be determined computationally. FIG. 4 shows a flowchart for reconstructing image data with scatter correction. First, in step MEAS, the measurement data generated during a CT measurement of an examination object are acquired. Following the measurement a first image PIC0 of the examination object is reconstructed from the raw data, i.e. without scattered radiation correction. From the estimated image PIC0, which contains image artifacts due to the scattered radiation present, the scattered radiation signal STREU is determined for each detector element. In the following step KOR, the measurement data are corrected using the scattered radiation signal STREU. The correction is accomplished essentially in that the scattered radiation intensity calculated for each detector element is subtracted from the raw data. An improved image PIC1 of the examination object is reconstructed using the measurement data corrected in step KOR.

The images PIC0 and PIC1 can be two-dimensional sectional images or three-dimensional volume images. Image reconstruction methods known per se can be used for reconstructing the images PIC0 and PIC1.

Monte Carlo simulations could be used in order to determine the scattered radiation signal STREU. In this case it is assumed that the examination object has an attenuation distribution according to the estimated image PIC0. The probability that the beam will be scattered in specific directions can now be calculated for each beam. This permits an exact calculation of the scattered radiation signal STREU, though it is very computationally intensive. Multiple scatterings must namely be taken into account in order to attain the high level of accuracy that is necessary for CT images. This means that after a first scattering at or in the examination object a beam can experience further scattering inside the object, etc. Within the context of the Monte Carlo simulation this corresponds to a cascaded application of the beam tracking through the examination object; very many beams must therefore be calculated.

Figure 5:
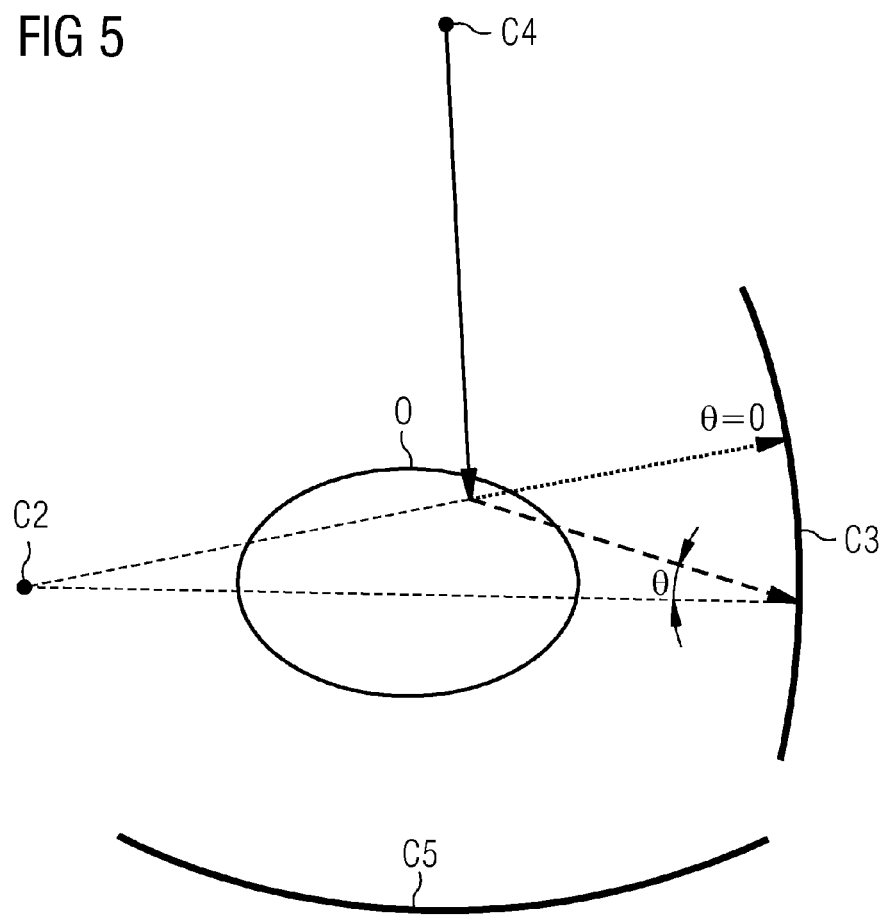
FIG. 5: shows an illustration of geometric relationships during the cross scattering.

In order to avoid these disadvantages, a model MOD of a scatter kernel is determined independently of the actual examination object. In order to explain the variables used during the model creation, FIG. 5 illustrates the geometric relationships in the cross scattering. As in FIG. 3, the x-ray source/detector pair C2 and C3 can be seen, together with the x-ray source/detector pair C4 and C5. As in FIG. 3, the diagram represents a two-dimensional axial section through the examination object O. The continuous arrow stands for a beam which emanates from the x-ray source C4. The beam is scattered at a point within the examination object O. A point at which scattering takes place is understood in the following to mean a surface or volume element of the examination object.

The dotted arrow shows how the beam is scattered at this point in such a way that it is incident on the detector C3 at the angle θ=0. The direction θ=0 points to the so-called midday channel; this is that detector element on which an incident beam stands at a 90° angle. This beam direction corresponds to the connecting line between the midday channel and the associated x-ray tube C2. Each scatter point within the examination object can therefore be assigned a midday channel. The dashed arrow shows how the beam is scattered at the same point within the examination object in such a way that it is incident on the detector C3 with the direction θ.

Figure 6:
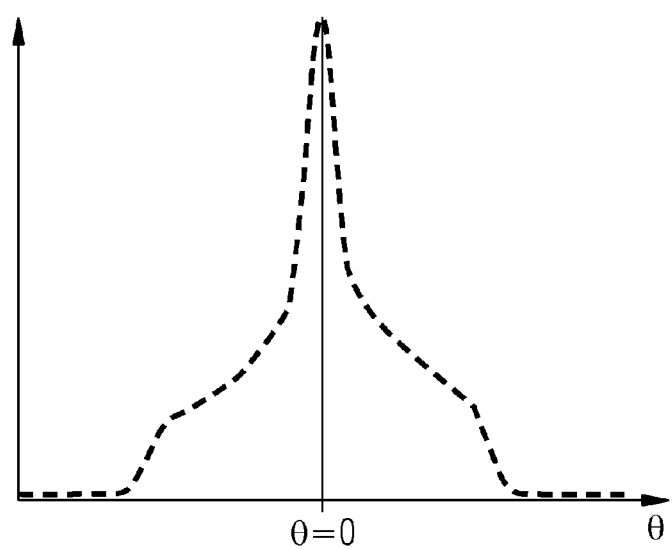
FIG. 6: shows an angle-dependent scatter distribution of a single scattering point (voxel) for a specific value of the line integral from the scatter point to the detector element.

The model MOD of a scatter kernel is determined with the aid of a model-like examination object. For example, a water-filled cylinder which is arranged symmetrically on the z-axis of the CT device can be used as the model-like examination object. A scattered beam distribution is determined for a specific point within the model-like examination object; this is dependent on two variables. The first variable is the angle θ, at which a beam scattered at the point under consideration lies with respect to the surface normal of the detector element under consideration. FIG. 6 shows such a scattered beam distribution. The intensity of the scattered radiation is plotted on the vertical as a function of the angle θ. The maximum is located at the angle θ=0, i.e. at the point where the scattered beam is incident on the midday channel. The reason for this is that the detector geometry is already incorporated into the scattered beam distribution, according to which because of the collimators the detector is easier to reach by beams at the angle θ=0 than at other angles. It is therefore already a matter of a realization-related representation into which the realization of the detector is incorporated. The scattered beam distribution does not have to be necessarily symmetrical around the value θ=0. In the event that no cross scattering, but only forward scattering is present, a symmetrical scattered beam distribution is given.

The second variable on which the scattered beam distribution of the considered point of the model-like examination object depends is the line integral of the attenuation values starting from the scatter point to that detector element on the detector arc over which the considered scatter point stands at a 90° angle, in other words to the midday channel. In order to calculate this variable, the—generally location-dependent—attenuation coefficient is integrated within the examination object along the line from the scatter point to the midday channel. A scattered beam distribution dependent on the angle θ according to FIG. 6 is determined for different values of the line integral. It generally applies that the scattered beam distribution varies with the value of the line integral in such a way that the maximum of the scattered beam distribution at θ=0 becomes smaller and the curve wider as the value of the line integral increases. The reason for this is that more x-ray quanta are absorbed and scattered at greater values of the line integral along the section.

The reason for using a variable in the form of the line integral from the scatter point to the midday channel lies in the fact that the scattering in the direction of the midday channel contributes most to the scatter signal (see FIG. 6). Although it would be more accurate to take other line integrals into account as well, the computational overhead, both for determining the model MOD and subsequently at the time of the image reconstruction for calculating the scattered radiation signal STREU, would be greater.

In order to determine the scattered beam distributions for different values of the line integral, the model-like examination object is modified based on consideration of different thicknesses of the model-like examination object. If, as in the above-cited example, a water-filled cylinder is used as the model-like examination object, then cylinders of different diameters are considered. In this case, however, the scatter point should always remain the same, i.e. the same scatter point is considered in each case in relation to the center of the cylinder.

The scattered beam distributions of the scatter point within the model-like examination object can be determined in different ways:

In the case of the Monte Carlo simulation, a statistical approach is adopted.

In the case of an analytical determination, the scattered beam distributions are calculated exactly.

In the case of the experimental determination, the model-like examination object is actually measured. Here, the geometry of the experimental setup is the same as or similar to the simulation. This can be realized e.g. by way of a small target at which a pencil beam is aimed directly and which is embedded into surrounding material, e.g. into a real water cylinder.

As result, the model MOD of a scatter kernel is present as a function dependent on the two variables line integral and θ. The values of the function can be stored in a table or the like. The model MOD can be determined prior to the data acquisition MEAS (FIG. 4) so that the model MOD will already be available when an image of the examination object is to be reconstructed.

The model MOD is now used in order to determine the scattered radiation signal STREU in relation to the real examination object from the estimated image PIC0. On account of the estimated image PIC0, an attenuation value is present for every point within the examination object, which means that it is possible to determine the value of the line integral starting from the respective point to the midday channel. Thus, a scattered beam distribution according to FIG. 6 can be assigned to every point within the examination object. This is accomplished in that the respective line integral is determined and a search made for the associated curve of the model MOD. This search can be realized e.g. by reading out from a table. Where necessary interpolation or extrapolation can be used if no value of the model MOD is present in relation to a calculated line integral value.

Once the angle-dependent scattered beam distributions are available for each image point (pixel) of the examination object, the scattered radiation signal STREU can be determined for each detector element. Toward that end the contributions of all image points relating to the considered detector element are added. This addition is preferably weighted, e.g. based on a weighting using the distance between the scatter point and the considered detector element. For geometric reasons a $1/r2$ weighting is suitable for this, such that an increasing distance leads to a smaller weight of the respective image point in the summation. An additional weighting possibility is to take into account the material at the location of the respective image point; thus, for example, different scatter intensities can be assumed for bone than for soft tissue.

The scattered radiation signal STREU obtained hereby per detector element can now be used for correcting the raw data. The image PIC1 obtained from the corrected measurement data can be output as a result image. Alternatively hereto it is possible to perform further iterations in order to obtain an even better image. Toward that end an improved scattered radiation signal STREU would be calculated from the image PIC1 using the model MOD, and this would be used in turn for correcting the measurement data and subsequent image calculation. In this way iteration images can be calculated until a specific abort criterion is met.

A significant advantage of the approach described is that the model MOD only has to be calculated once and subsequently can be used for reconstructing a plurality of images of different examination objects. Because the calculation of the model MOD can be completed in advance of the image reconstruction, the latter can be executed more quickly and with less computational overhead. Within the scope of the image reconstruction it is namely necessary, in order to determine the scattered radiation signal STREU, merely to refer to the scattered beam distributions of the image points in a lookup table or similar and to perform the addition detector element by detector element. In contrast to the aforementioned possibility of obtaining the scattered radiation signal STREU from the estimated image PIC0 by way of a Monte Carlo simulation, the explained image reconstruction is not only quicker, but also leads to a reduction in variance compared with the image-based Monte Carlo method. If the model MOD is obtained from a model-like examination object with the aid of a Monte Carlo method, the explained method represents a hybrid between a Monte Carlo method and a model method.

So far the case has been described whereby the model MOD contains the line integral from the scatter point to the midday channel and the angle θ as variables. It is also possible to incorporate further variables into the model MOD. Suitable examples hereof are:

The fan angle of the incident beam, in other words the angle of the incident beam in relation to a beam which leaves the x-ray source at a 90° angle, and the fan angle of the midday channel, in other words the angle between the midday channel beam and the beam which strikes the center of the detector at a 90° angle.

In order to take account of the variables, the model-like examination object can be displaced both in a transverse direction with respect to the incident central beam and at the same time also in a direction parallel to the incident central beam. This enables the range of the scatter angles taken into account to be extended.

The integral already penetrated by the incident beam.

Because the beam has already passed through material within the object, its spectrum also changes at the considered scatter point in addition to its intensity. In order to take this dependency into account, the model-like examination object can be modified in such a way that material of different thickness is still located ahead of the considered scatter point. The spectrum of the radiation incident on the scatter point is taken into account by way of the variable.

A relation between the line integral to the midday channel and the line integral to one or more other detector channels.

This allows the dependency of the scattered radiation distribution on the shape of the object to be taken into account. This is because different secondary scattering processes take place depending on the shape and thickness of the traversed material from the scatter point to the respective detector channels. By way of this variable, therefore, the scattering object can be characterized more accurately and its properties accordingly taken into account in the calculation of the scattered radiation signal.

In order to take this variable into account, the scatter point can be displaced within the model-like examination object.

The attenuation value of the scatter point and/or the attenuation values of the material surrounding the scatter point.

In order to take this variable into account, the scatter point can be regarded as including different materials, or different materials surrounding the scatter point are used. For example, other fillings of the cylinder can be considered instead of a cylinder filled with water.

The number of variables used for the model MOD and the variables chosen from the above-cited possibilities depend on the desired level of accuracy. Obviously the computational overhead increases in proportion to the increase in the number of variables both for determining the model MOD and for determining the scattered radiation signal STREU. It is of course possible to determine the model MOD with more variables than will subsequently be used in the determination of the scattered radiation signal STREU; in this case the variables not used are set to a suitable constant value during the determination of the scattered radiation signal STREU.

The approach described is suitable both for CT devices having only one x-ray source, i.e. in order to eliminate the consequences of forward scattering, and for systems having two or more source/detector pairs.

The example embodiments described hereinabove relate to the medical application of the invention. However, the invention can also be used in fields outside of medicine, for example in baggage checking or materials analysis.

The invention has been described hereintofore with reference to an example embodiment. It is understood that numerous variations and modifications are possible without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing image data of an examination object from measurement data, the measurement data being previously acquired in the course of a relative rotational movement between a radiation source of a computed tomography system and the examination object, the method comprising:
    reconstructing first image data of the examination object from the measurement data;
    calculating scatter signals from the first image data using a scattered radiation model, the scattered radiation model specifying an angle-dependent scatter distribution for a scatter point as a function of a line integral corresponding to an attenuation integral of a scattered beam from the scatter point to a specific detector element,
    the calculated scatter signals being used for correcting the measurement data; and
    reconstructing second image data using the corrected measurement data.

2. The method of claim 1, wherein the specific detector element is that detector element on which the scattered beam is incident at a 90° angle.

3. The method of claim 1, wherein, in order to calculate the scatter signal for a detector element for each scatter point of the examination object using the first image data, a line integral corresponding to an attenuation integral of a beam from the respective scatter point to the respective detector element being calculated and assigned to an angle-dependent scatter distribution of the scattered radiation model.

4. The method of claim 3, wherein, in order to calculate the scatter signal for the detector element, the detector-element-related contributions of the scatter distribution of a plurality of scatter points of the examination object are added together.

5. The method of claim 4, wherein in the addition, a weighting is applied as a function of the respective distance between the scatter point and the detector element.

6. The method of claim 1, wherein the scattered radiation model is determined using a model-like examination object.

7. The method of claim 6, wherein the model-like examination object is a water-filled cylinder.

8. The method of claim 6, wherein the scattered radiation model is determined using a Monte Carlo simulation.

9. The method of claim 6, wherein the scattered radiation model is determined using measurements taken on the model-like examination object.

10. The method of claim 1, wherein the scattered radiation model is used to calculate scatter signals from the second image data, the calculated scatter signals are used for correcting the measurement data, and third image data are reconstructed using the corrected measurement data.

11. The method of claim 1, wherein
    according to the scattered radiation model, the angle-dependent scatter distribution is additionally dependent on at least one of
        the angle between the beam incident at the scatter point and the beam scattered to the specific detector element,
        the fan angle of the beam incident at the scatter point within a bundle of rays emitted by the radiation source,
        the fan angle of the specific detector element inside the detector,
        the angle between the beam scattered to the specific detector element and a beam incident at a 90° angle to the center of the detector,
        a line integral corresponding to an attenuation integral of the beam incident at the scatter point up to the scatter point,
        a relation between the line integral corresponding to an attenuation integral of the scattered beam from the scatter point to the specific detector element and a line integral corresponding to an attenuation integral of the scattered beam from the scatter point to another detector element,
        the attenuation value of the scatter point according to the first image data, and
        at least one attenuation value of the material surrounding the scatter point according to the first image data.

12. The method of claim 1, wherein the measurement data were acquired in the course of a simultaneous relative rotational movement between a first radiation source and the examination object and a second radiation source and the examination object, and wherein the scatter signals are calculated in relation to two detectors assigned to the respective radiation sources.

13. A computing unit for reconstructing image data of an examination object from measurement data of a CT system,
    said computing unit comprising a memory storing program code for performing the method of claim 1 when executed on the computing unit.

14. A CT system comprising the computing unit of claim 13.

15. A non-transitory computer readable medium comprising a computer program including program code for performing the method of claim 1 when the computer program is executed on a computer.

16. A non-transitory computer-readable data medium containing program code of a computer program for performing the method of claim 1, when the computer program is executed on a computer.

17. The method of claim 1, wherein, in order to calculate the scatter signal for a detector element for each scatter point of the examination object using the first image data, a line integral corresponding to an attenuation integral of a beam from the respective scatter point to the respective detector element being calculated and assigned to an angle-dependent scatter distribution of the scattered radiation model.

18. The method of claim 17, wherein, in order to calculate the scatter signal for the detector element, the detector-element-related contributions of the scatter distribution of a plurality of scatter points of the examination object are added together.

19. The method as claimed in claim 18, wherein in the addition, a weighting is applied as a function of the respective distance between the scatter point and the detector element.

20. The method of claim 7, wherein the scattered radiation model is determined using a Monte Carlo simulation.

21. The method of claim 7, wherein the scattered radiation model is determined using measurements taken on the model-like examination object.

* * * * *